United States Patent
Boot

(10) Patent No.: US 7,308,893 B2
(45) Date of Patent: Dec. 18, 2007

(54) METERED DOSE DISPENSERS AND ASSEMBLIES THEREFOR

(75) Inventor: Deryck Boot, Leicestershire (GB)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/596,328

(22) PCT Filed: Nov. 2, 2004

(86) PCT No.: PCT/US2004/036450

§ 371 (c)(1),
(2), (4) Date: Jun. 9, 2006

(87) PCT Pub. No.: WO2005/060441

PCT Pub. Date: Jul. 7, 2005

(65) Prior Publication Data

US 2007/0079828 A1    Apr. 12, 2007

(30) Foreign Application Priority Data

Dec. 10, 2003  (GB) ............................ 0328502.0

(51) Int. Cl.
*A61M 15/00* (2006.01)
*A61M 11/00* (2006.01)

(52) U.S. Cl. ............. 128/203.15; 604/97.03; 215/230; 428/40.1; 128/200.23

(58) Field of Classification Search .......... 128/200.23, 128/203.15, 203.23; 215/230, 901, 252, 215/258, 329, 201, 203, 365; 220/214, 319, 220/288; 206/459.1, 459.5, 534, 807; 40/310, 40/299.01; 222/74; 604/97.03; 428/40.1
See application file for complete search history.

(56) References Cited

U.S. PATENT DOCUMENTS

| 1,360,729 | A | * | 11/1920 | Darmis ........................ 84/263 |
| 2,161,561 | A | * | 6/1939 | Dalton ........................ 215/246 |
| 4,921,277 | A | * | 5/1990 | McDonough ................. 283/81 |
| 5,622,163 | A | | 4/1997 | Jewett et al. |
| 5,722,547 | A | * | 3/1998 | Shankland ................... 215/230 |
| 5,871,007 | A | | 2/1999 | Clark, Jr. |
| 6,283,365 | B1 | | 9/2001 | Bason |
| 6,613,410 | B1 | | 9/2003 | Sellars |
| 2005/0209558 | A1 | * | 9/2005 | Marx ....................... 604/97.03 |

FOREIGN PATENT DOCUMENTS

| EP | 1 369 139 A1 | 12/2003 |
| WO | WO95/08484 | 3/1995 |
| WO | WO95/26769 | 10/1995 |
| WO | WO96/03172 | 2/1996 |
| WO | WO96/39337 | 12/1996 |
| WO | WO98/56444 | 12/1998 |
| WO | WO99/57019 | 11/1999 |

* cited by examiner

*Primary Examiner*—Justine R. Yu
*Assistant Examiner*—Shumaya Ali
(74) *Attorney, Agent, or Firm*—Ted K. Ringsred

(57) ABSTRACT

A dispensing canister-add-on-component assembly, comprising a dispensing canister comprising a substantially cylindrical container having a closed end and an open end, said open end of the container being equipped by means of a ferrule with a dispensing means; a substantially cylindrical add-on component; said component being positioned adjacent to the closed end of the container to form a generally cylindrical canister-component sub-assembly having an interface between the canister and add-on component.

8 Claims, 3 Drawing Sheets

METERED DOSE DISPENSERS AND ASSEMBLIES THEREFOR

FIELD

The present invention relates to assemblies of dispensing canisters with add-on-components (in particular dose counters) and dispensers, in particular metered dose dispensers, comprising such assemblies as well as methods of affixing an add-on component, such as a dose counter, to a dispenser canister.

BACKGROUND

Metered dose dispensers, in particular pressurized metered dose dispensers, have had a major role in for example the treatment of asthma and other conditions since they were introduced nearly half a century ago. Moreover, the use of metered dose medicinal dispensers is becoming an increasingly important method of administering medicaments to a patient e.g. to the lung, nasal and/or buccal cavities or sublingually.

The medicament is generally formulated with suitable propellant and if appropriate other components and charged into a container, e.g. an aerosol vial. The container is typically fitted by means of a ferrule with a dispensing means, such a valve, in particular a metered dose valve, comprising an elongate outlet member (e.g. a valve stem) movable between closed and discharged positions, to provide a dispensing canister. The dispensing canister is typically used in conjunction with an actuator, typically having a patient port, for example a mouthpiece or a port adapted for nasal use. The actuator typically comprises a support block having a socket adapted to receive the outlet member of the dispensing means and an orifice having open communication with the socket and the patient port. The container and the support block are reciprocally movable relative to each other to allow the outlet member to move to its discharge position during the operation or firing of the device, thereby dispensing a dose. The adaptor also typically includes an elongate or generally cylindrical portion extending opposite the support block and providing a chamber to house at least a portion of the container. To facilitate locating and supporting the proper alignment of the container within the chamber, typically the chamber is provided with one or more ribs. There are many critical design features of the actuator and the dispensing canister, in particular in relation to one another, in order to achieve the necessary and/or desirable medicinal dispensing performance. For example, for metered dose inhalers, the design of the airflow passage through the actuator entraining the spray is taken into account to facilitate the provision of the required and/or desired and/or consistent in vitro dose delivery and respirable fraction.

A difficulty arising from use of metered dose medicinal devices is that the patient often cannot precisely determine the amount of medicament in the container at any given time. In extreme cases, a patient, possibly in an emergency situation and requiring an immediate dose of medicament, may find that the container will not dispense a dose because its contents have already been exhausted.

A number of dose counters, as an add-on component for metered dose medicinal products to be mounted onto the closed end of the container of the dispensing canister, have been proposed, e.g. in WO 95/26769, WO 95/08484, WO 96/03172, WO 96/39337, WO 99/57019, U.S. Pat. No. 5,622,163 and U.S. Pat. No. 5,871,007.

SUMMARY OF THE INVENTION

Although dose counters as an add-on component to be mounted onto the closed end of the container provide an attractive possibility of retrofitting existing metered dose medicinal dispensing product designs or such product designs in their last stages of development with a dose counter, we have found that there are considerable difficulties in the practicalities of manufacture or in the provision of a robust assembly that allows incorporation of add-on components in such a way as not to interfere with the finely tuned product characteristics. For example, we have found that during manufacture (in a production line) the use of adhesives applied the closed end of the container to attach the dose counter can lead to contamination of the counting mechanism, or worse contamination of the dispensing means, thus leading to performance failure of the dose counter and/or dispensing means. Further, attachment via means such as crimping, gripping or thread-engaging skirts, annular clamps, etc. necessitate a re-design of the actuator and/or the dispensing canister and thus significant product development to assure proper coordination or tuning of the individual components and to achieve the necessary and/or desired performance characteristics of the dispensing product. Thus there is an ongoing need to provide a dispensing canister-dose counter assembly in which the dose counter, as add-on component, is securely attached onto the closed end of the canister and at the same time overcomes the difficulties associated with using adhesives in manufacturing and re-designing the dispensing canister and/or the actuator adapted to receive the dispensing canister.

One aspect of the present invention is the provision of a dispensing canister-add-on-component assembly, comprising a dispensing canister comprising a substantially cylindrical container having a closed end and an open end, said open end of the container being equipped by means of a ferrule with a dispensing means;

a substantially cylindrical add-on component; said component being positioned adjacent to the closed end of the container to form a generally cylindrical canister-component sub-assembly having an interface between the canister and add-on component; and an adhesive-backed film; said film being mounted circumferentially about the canister-component sub-assembly and adhered to an external surface of the container and an external surface of the add-on component, such that the film extends across the canister-component interface with its upper edge located about the add-on component and its lower edge about the container in the vicinity of the upper edge of the ferrule; and wherein said adhesive-backed film comprises at least two sections, a first section beginning near or substantially at said upper edge and extending across the canister-component interface towards the lower edge of the film and a second section beginning substantially at said lower edge extending towards the upper edge of the film and ending at or prior to said first section, wherein the first end region of the first section of the film overlaps the second end region of the first section of the film and the end regions of the second section of the film do not overlap.

It has been surprisingly found that an add-on component positioned over the closed end of the container can be securely affixed to the container using an adhesive-backed film as described to provide a robust dispensing canister-add-on-component assembly without the need of applying adhesive between the closed end of the container and the dose counter or the use of other types of other means of attachment. By applying the adhesive-backed film circumferentially about the dispensing canister-add-on-component (positioned but un-affixed) subassembly and providing an overlap in the first section of the film extending over the canister-component interface, the add-on component is securely and stably affixed to the container. The second section of the adhered film facilitates the overall robustness and tamper-resistibility of the assembly, and furthermore because the second section has no overlap the dispensing canister-add-on-component assembly can be advantageously used with an actuator adapted to receive the dispensing canister without interference with internal structures of the actuator, such as ribs.

Thus another aspect of the present invention is the provision of a dispenser for dispensing doses of medicament comprising a dispensing canister-add-on-component assembly as described herein and an actuator comprising an elongate or generally cylindrical portion defining an open-ended chamber, the dispensing canister of the dispensing canister-add-on-component assembly being received by the adaptor, wherein at least a portion of the container and the second section of the adhesive-backed film about said container is in part or completely located within said chamber.

While dispensing canister-add-on-component assemblies and dispensers described herein are particularly advantageous with the application of a dose counter as the add-on component, said assemblies and dispensers may be desirable for use with other types of add-on components, such as container extenders, button timers, etc.

The dispenser is typically a metered dose dispenser, more particularly a pressurized metered dose dispenser, such as a metered dose inhaler.

An additional aspect of the present invention is the provision of an adhesive-backed film for affixing a substantially cylindrical add-on component onto the closed end of a substantially cylindrical container of a dispensing canister, the adhesive-backed film comprising two sections, a first section beginning near or substantially at the upper edge and extending towards the lower edge of the film and a second section beginning substantially at the lower edge extending towards the upper edge of the film and ending at or prior to said first section, wherein the length of the width of the first section is greater than the length of the circumference of the container and the length of the width of the second section is equal to or less than the length of the circumference of the container.

The surface of the adhesive-backed film facing outwardly from the dispensing canister-component sub-assembly may be printable. This is advantageous in that the surface may then be printed with indicia, e.g. exhibiting product information concerning product. The film of the adhesive-backed film may be made of a paper or a polymer, more suitably a polymer. For ease in manufacturing, the adhesive is desirably a pressure sensitive adhesive.

A further aspect of the present invention is the provision of a method of affixing an add-on component, said component being substantially cylindrical, onto a dispensing canister comprising a substantially cylindrical container having a closed end and an open end, said open end of the container being equipped by means of a ferrule with a dispensing means, said method comprising the following steps:

a) positioning the add-on component adjacent to the closed end of the container to form a generally cylindrical canister-component sub-assembly having an interface between the canister and add-on component;

b) providing an adhesive-backed film as described herein;

c) mounting an adhesive-backed film circumferentially about the canister-component sub-assembly and adhering the adhesive-backed film to an external surface of the container and an external surface of the add-on component, such that the upper edge of the film is located about the add-on component and the lower edge of the film about the container in the vicinity of the upper edge of the ferrule, and such that the first section of the film extends across the canister-component interface with the first end region of the first section of the film overlapping the second end region of the first section of the film, while the end regions of the second section of the film do not overlap.

These and other features, aspects and advantages of the present invention will become better understood in the following description, appended claims and accompanying drawings.

DETAILED DESCRIPTION

It is to be understood that the present invention covers all combinations of particular, desirable and preferred aspects of the invention described herein.

Figure 1:
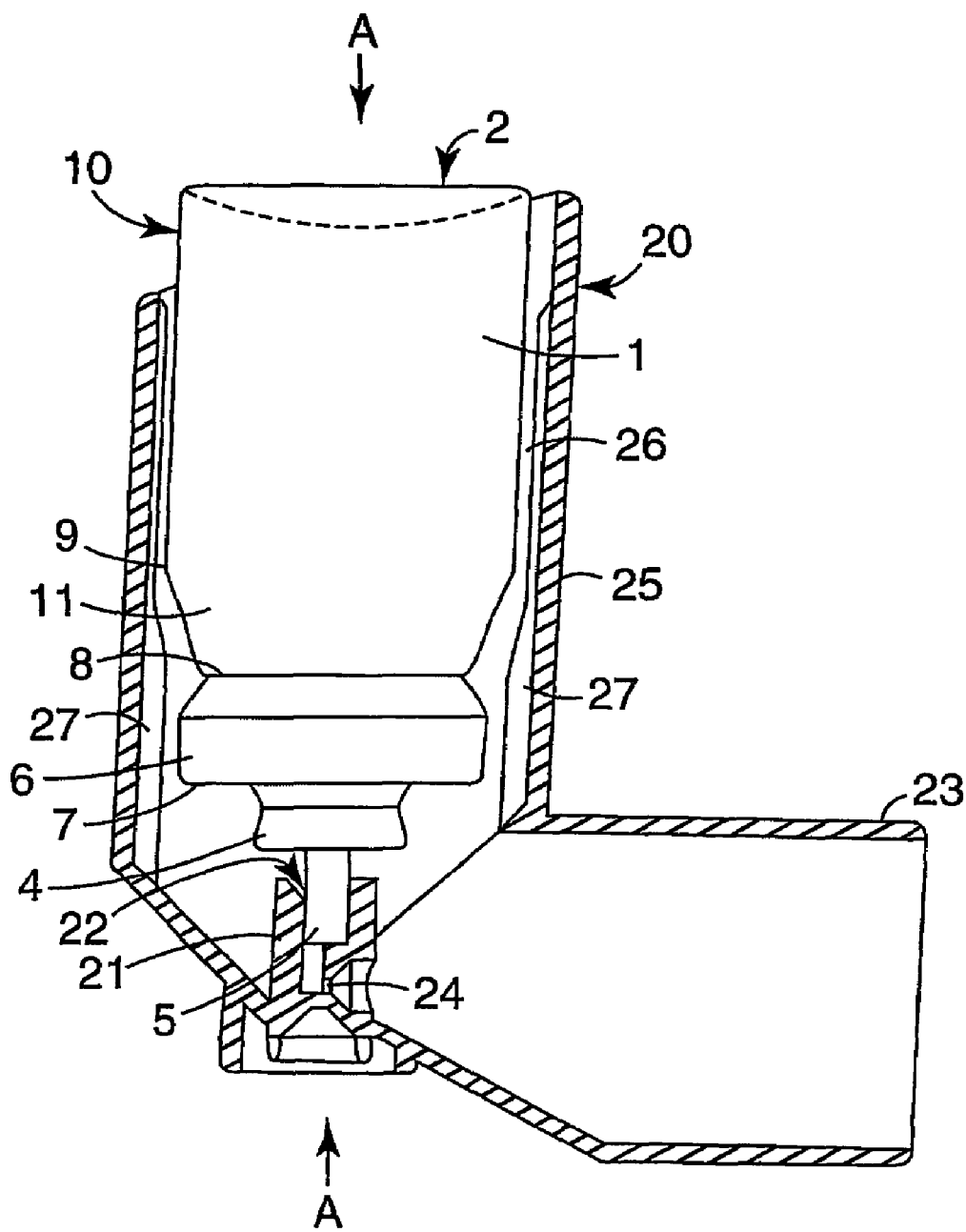
FIG. 1 shows a vertical, in part cross-sectional, view of an exemplary dispenser, in particular a conventional press-and-breath-type of pressurized metered dose inhaler.

For better understanding of the various aspects of the present invention, an exemplary conventional dispenser without an add-on-component will be initially described. In FIG. 1 an exemplary dispenser, in particular a pressurized metered dose inhaler, is illustrated. The dispenser comprises a dispensing canister (10) and an actuator (20). The dispensing canister typically comprises a substantially cylindrical container (1), in particular an aerosol container, having a closed end (2), which is typically concave in form, and an open end (3, not visible). The open end of the container is equipped with a dispensing means (4), in particular, a dispensing valve, more particularly a metering dose valve, having an elongate outlet member (5), in particular a valve stem, movable between closed and discharged positions. The dispensing means is normally mounted onto the container by means of a ferrule (6). The ferrule is typically fastened onto the container by crimping, however it can be suitably fastened onto the container by other means, such as welding, adhesives, snap-fit, thread-fit. The term ferrule is understood here to mean any component or element of the dispensing canister, which is used to allow the attachment of the dispensing means to the container. The ferrule may be an integral component of the dispensing means or an integral component of the container or alternatively be a separate component, e.g. in the form of a mounting ring or cup. After fastening (e.g. crimping), the ferrule typically shows a seal-edge (7) (e.g. a folded edge) near the open end of the container and an upper edge or boundary (8) (e.g. a crimped edge) about the container. The container (1) may have a constricted portion (11) adjacent to the upper edge of the ferrule with the container then having a shoulder (9) in the vicinity of the upper edge of the ferrule. The adaptor (20) typically comprises a support block (21) having a socket (22). The outlet member (5) of the dispensing-canister (10) (e.g. the dispensing end of the elongate valve stem of a metered dose dispensing valve) is received by the socket (22) and thus positioned in the support block (21). The container (1) and the support block (21) are reciprocally movable relative to each other along an axis, marked as "A". The adaptor typically includes a patient port, such as a mouthpiece (23) and the support has an orifice (24) having open communication with the socket and the mouthpiece (23). The adaptor also typically includes an elongate or generally cylindrical portion (25) extending opposite the support block defining a chamber (26) to accommodate at least a portion of the container (1) of the dispensing-canister. One or more ribs (27) positioned within the chamber of the cylindrical portion aid in locating and supporting the container in the correct position.

Figure 2:
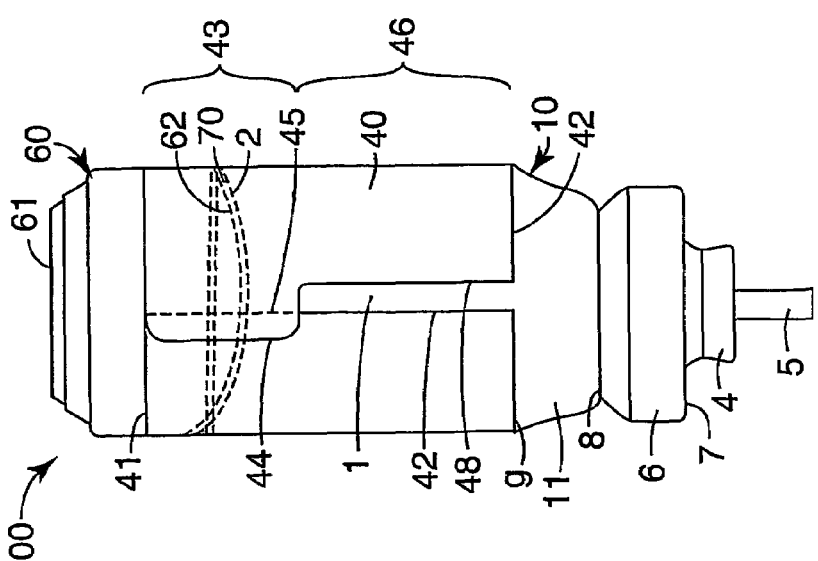
FIG. 2 shows a vertical view of an embodiment of a dispensing canister-add-on-component assembly in accordance with the invention.
Figure 3A:
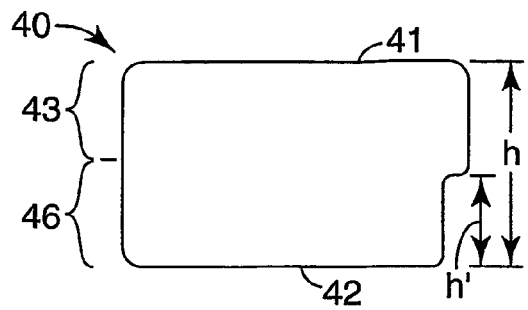
FIGS. 3a to e show top views of various embodiments of adhesive-backed films in accordance with the present invention.
Figure 3B:
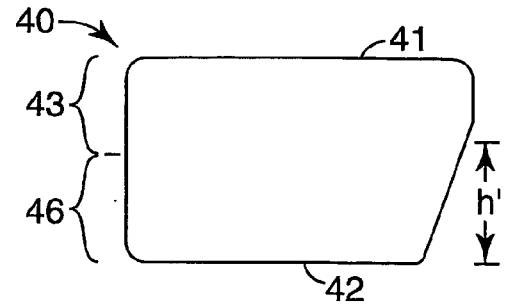
Figure 3C:
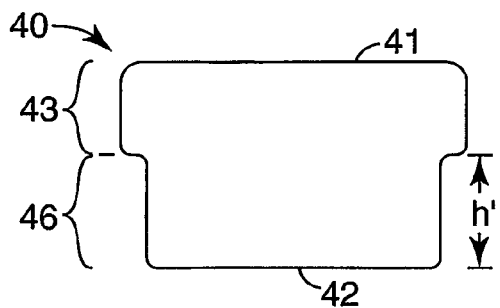
Figure 3D:
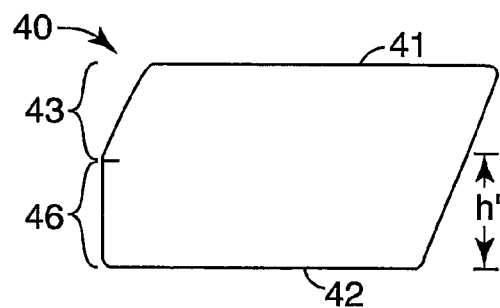
Figure 3E:
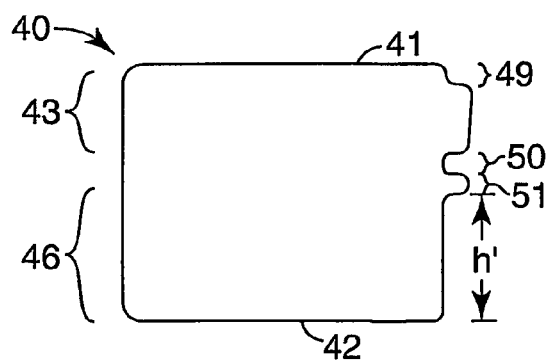

The dispensing canister-add-on-component assembly in accordance with present invention comprises a dispensing canister, an add-on component and an adhesive-backed film. This is best understood by referring to FIG. 2 illustrating an embodiment of such an assembly. As can be seen in the illustrated assembly (100) the add-on component (60), which is substantially cylindrical, is positioned adjacent to the closed end (2) of the container (1) of the dispensing canister (10), which is substantially cylindrical, to form. a generally cylindrical canister-component sub-assembly having an interface (70) between the canister and the add-on component.

Suitable add-on components can be any type of substantially cylindrical add-on component positionable adjacent to the closed end of a dispensing canister container, in particular (mechanical or electronic) dose counters. Under the term "add-on-component" as used hereafter it understood to include a dose counter as a preferred add-on-component. Desirably, the diameter of the add-on component is equal to or substantially equal (e.g. ±5%) to the diameter of the container at the closed end of the container. To facilitate positioning of the add-on component, e.g. during manufacturing and/or converting, and/or to facilitate the subsequent affixing of the add-on component onto the container, the closed end of the container and the base of the add-on component are advantageously profiled to mate together. For example, the closed end of a dispensing canister container is typically concave, thus it is advantageous that the base on the add-on component has a corresponding convex form. Desirably, the boundaries of the mating surfaces, i.e. the closed end of the container and the base of the add-on component, are arranged such that any gap at the canister-component interface is a minimal.

In the embodiment shown in FIG. 2, the illustrated add-on component (60) is a dose counter of the type disclosed in WO 99/57019 with an actuation button (61) and a display (not shown) indicating the dose counts or usage of the dispenser. The base (62) on the add-on component has a desirable convex form, while the closed end (2) of the container is concave in form. The open end of the container (1) is equipped with a dispensing means (4) secured by a ferrule (6).

The dispensing means is suitably a dispensing valve, more particularly a metering dose valve, having an elongate outlet member, in particular a valve stem, movable between closed and discharge positions.

Referring again to the embodiment shown in FIG. 2, the adhesive-backed film (40) is mounted circumferentially about the canister-component sub-assembly and adhered to an external surface of the container (1) and an external surface of the add-on component (60). The upper edge (41) of the adhesive-backed film is located about the add-on component and the lower edge (42) in the vicinity the upper edge (8) of the ferrule (6), more particularly near a shoulder (9) of the container. The film (40) thus extends across the canister-component interface (70). The adhesive-backed film in the assembly shown in FIG. 2 has two sections, the first section (43) beginning substantially at the upper edge (41) and extending across the canister-component interface (70) towards the lower edge of the film. The second section (46) begins substantially at the lower edge (42) and extends towards the upper edge of the film, ending at the lower boundary of the first section. As can be seen in FIG. 2, one end region (44) of the first section (43) of the film overlaps the other end region (45) of the first section, while the end regions (47,48) of the second section of the film do not overlap.

It is to be appreciated that while the adhesive-backed film comprises at least two sections, a first section beginning near or substantially at said upper edge towards the lower edge of the film and a second section beginning substantially at said lower edge extending towards the upper edge of the film and ending at or prior to said first section, the film may include additional sections located for example between the first and second sections and/or between the upper boundary of the first section and the upper edge of the film.

This can be better understood by reference to FIG. 3 (a) to (e), showing a top view of a number of embodiments of adhesive-backed films suitable for use for affixing an add-on component onto the closed end of a substantially cylindrical container of a dispensing canister. Each of the embodiments of adhesive-backed film depicted in FIG. 3 has an upper and lower edge (41, 42) and a first and second section (43, 46). The embodiment shown in FIG. (e) has two additional sections (50, 51) located between the first and second sections (43, 46) as well as a section (49) adjacent to the first section towards the upper edge (41). As can be appreciated from the illustrated embodiments the corners of the film and respective sections thereof are typically rounded-off. The width of the first section (43) (if applicable as its most narrow width) is greater than the width (if applicable as its greatest width) of the second section (46).

To assure overlap of the first section and non-overlap of the second section of the adhesive-backed film in the dispensing canister-add-on-component in the assembly, the length of the width (if applicable as its most narrow width) of the first section is greater than the length of the circumference of the container and the length of the width (if applicable at its greatest width) of the second section is equal to or less than the length of the circumference of the container. Desirably, the length of the width of the first section is more than about 2%, more desirable more than about 5% longer the length of the circumference of the container. Generally the length of the width first section is no more than about 10% longer than the length of the circumference of the container.

The selected and/or desired overall height from the upper edge to the lower edge of the adhesive-backed film (e.g. marked as "h" in FIG. 3a) depends on the dimensions of the particular dispensing canister-add-on-component subassembly. Typically an overall height is selected such that when the film is mounted circumferentially about the canister-component sub-assembly the upper edge will be located about the add-on component and the lower edge about the container in the vicinity of the upper edge of the ferrule. For containers having a shoulder in the vicinity the upper edge of the ferrule, desirably the lower edge will be located about the container near the shoulder. The selected and/or desired height of the second section of the adhesive-backed film (e.g. marked h' in FIG. 3a) typically depends on the dimensions of the particular dispensing-canister and actuator used to provide a dispenser, as discussed in more detail below.

Figure 4:
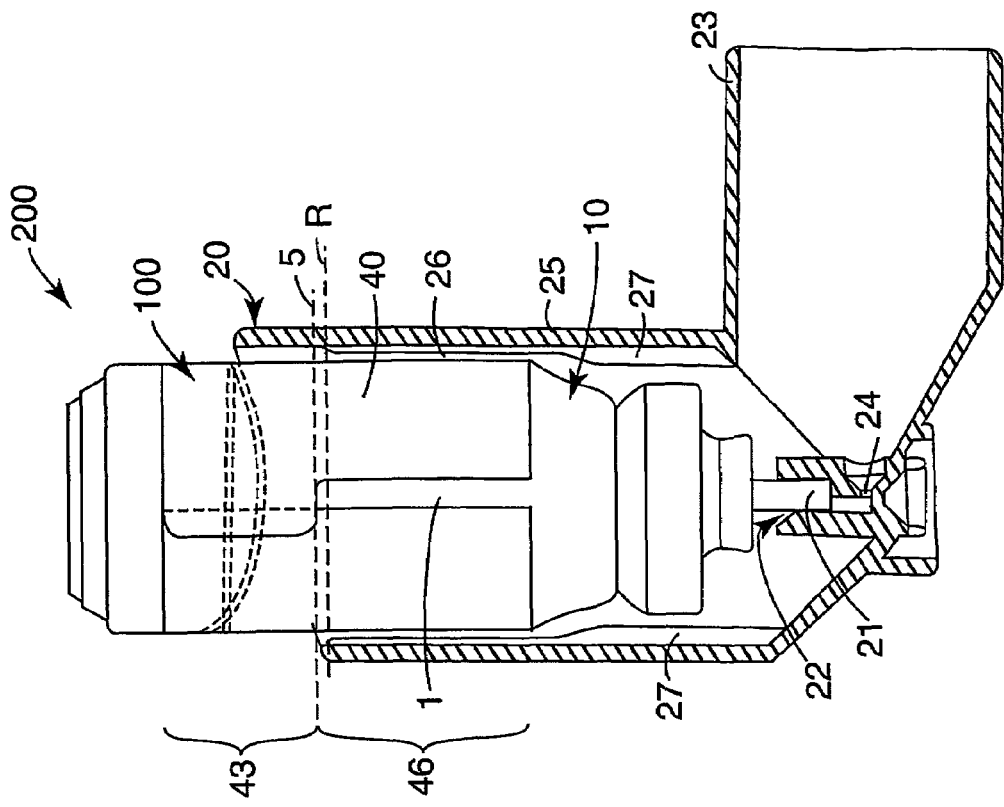
FIG. 4 shows a vertical, in part cross-sectional, view an embodiment of a dispenser in accordance with the invention comprising the dispensing canister-add-on-component assembly illustrated in FIG. 2.

Referring to FIG. 4, which illustrates an embodiment of a dispenser (200) in accordance with the invention, including a canister-add-on-component assembly (100) as shown in FIG. 2 an actuator (20) comprising an elongate or generally cylindrical portion (25) defining an open-ended chamber 26). The dispensing canister (10) of the canister-add-on-component assembly is received by the actuator (20). At least a portion of the container (1) and the second section (46) of the adhesive-backed film (40) about said container is in part located within the chamber. In other embodiments the complete second section may be located within the chamber.

In preferred embodiments, the chamber has on its internal surface one or more ribs (27) protruding inwardly and extending vertically towards the open end of the chamber. The end, if applicable as defined by the inner corner thereof, of the rib or ribs towards open end of the chamber defines a first horizontal position (marked "R" is the FIG. 4). For embodiments including two or more ribs of different lengths the uppermost end, and again if applicable as defined by the inner corner thereof, would then define said first horizontal position. As can be appreciated from FIG. 4, the upper boundary of the second section towards the closed end of the container defines a second horizontal position (marked "S"). The second section has a height (h'), such that the second horizontal position (S) is located at or above and does not fall below the first horizontal position (R) (in the direction of support block (21) of the actuator) when the dispenser is at rest and during actuation of the dispenser. By ensuring that the upper boundary of the second section of the adhesive-backed film is located at or extends beyond the end of the rib(s) (in the direction towards the closed end of the container), an interference and/or snagging of the adhesive-backed film, in particular at the seams of the overlapping regions thereof, can be minimized or eliminated upon insertion of the dispensing canister in the actuator, during actuation of the dispenser and upon any rotation of the assembly within the actuator.

It is to be understood that the actuator as well as the dispensing canister used in dispensers in accordance with the invention may suitably include any structural feature described in conjunction with the dispenser illustrated in FIG. 1.

Typically, the thickness of the adhesive-backed film is selected such that its outer surface remains free from contact to any internal structure located within the chamber of the actuator. Desirably, the thickness of the adhesive-backed film is 200 microns or less, more desirably 160 microns or less. To ensure stability and robustness of the dispensing canister-add-on-component assembly, the minimal thickness of the adhesive-backed film is desirably 40 micron or greater, more desirably 80 micron or greater.

The outer surface, i.e. the surface facing outwardly from the canister-component sub-assembly, of the adhesive-backed film is desirably printable. Advantageously, the outer surface of the adhesive-backed film is printed with indicia, e.g. concerning information about the dispensing product. The film is suitable made of a paper or a polymer. Suitable polymers include thermoplastic polymer, such as polyethylene, polypropylene, polyethylene terephthalate, polyvinyl chloride or cellulose acetate. Preferably the film is made of a high gloss opaque white polyethylene material. Suitably the film has a tensile strength of 10 N/mm$^2$ or higher. The basis weight of the adhesive-backed film may be in the range 50 to 100 g/m$^2$. The adhesive is desirably a pressure sensitive adhesive, such as an acrylic pressure sensitive adhesive.

The add-on-component is affixed to the container of the dispensing canister by positioning the add-on component adjacent to the closed end of the container to form a generally cylindrical canister-component sub-assembly having an interface between the canister and add-on component and mounting an adhesive-backed film circumferentially about the canister-component sub-assembly and adhering the adhesive-backed film to an external surface of the container and an external surface of the add-on component. The mounting and adhering of the adhesive-backed film about the positioned subassembly typically occurs simultaneously. The adhesive-backed film is mounted and adhered, such that the upper edge of the film is located about the add-on component and lower edge of the film about the container in the vicinity of the upper edge of the ferrule, and such that the first section of the film extends across the canister-component interface with the first end region of the first section of the film overlapping the second end region of the first section of the film, while the end regions of the second section of the film do not overlap.

It is to be appreciated that the dispensing canister-add-on-component assemblies and dispensers may incorporate a range of the adhesive-backed film forms, which could not exhaustively be illustrated here, without departing from the scope of the invention.

The invention claimed is:

1. A dispensing canister-add-on-component assembly, comprising a dispensing canister comprising a substantially cylindrical container having a closed end and an open end, said open end of the container being equipped by means of a ferrule with a dispensing means;

a substantially cylindrical add-on component; said component being positioned adjacent to the closed end of the container to form a generally cylindrical canister-component sub-assembly having an interface between the canister and the add-on component; and an adhesive-backed film; said film being mounted circumferentially about the canister-component sub-assembly and adhered to an external surface of the container and an external surface of the add-on component, such that the film extends across the canister-component interface with its upper edge located about the add-on component and its lower edge about the container in the vicinity of the upper edge of the ferrule; and wherein said adhesive-backed film comprises at least two sections, a first section beginning near or substantially at said upper edge and extending across the canister-component interface towards the lower edge of the film and a second section beginning substantially at said lower edge extending towards the upper edge of the film and ending at or prior to said first section, wherein the first end region of the first section of the film overlaps the second end region of the first section of the film and the end regions of the second section of the film do not overlap.

2. A dispensing canister-add-on-component assembly according to claim 1, wherein the add-on component is a dose counter.

3. A dispensing canister-add-on-component assembly according to claim 1, wherein the surface of the adhesive-backed film facing outwardly from the canister-component sub-assembly is printed with indicia.

4. A dispensing canister-add-on-component assembly according to claim 1, wherein the film of the adhesive-backed film is made of a paper or a polymer.

5. A dispensing canister-add-on-component assembly according to claim 1, wherein the adhesive is a pressure-sensitive adhesive.

6. A dispenser for dispensing doses of medicament comprising a canister-add-on-component assembly according to claim 1 and an actuator comprising an elongate or generally cylindrical portion defining an open-ended chamber, said dispensing canister of the dispensing canister-add-on-component assembly being received by the adaptor, wherein at least a portion of the container and the second section of the adhesive-backed film about said container is in part or completely located within said chamber.

7. A dispenser according to claim 6, wherein said chamber has on its internal surface one or more ribs protruding inwardly and extending vertically towards the open end of the chamber and the second section of the adhesive-backed film has a height, such that the horizontal position defined by the boundary of the second section towards the closed end of container is located at or above and does not fall below the horizontal position defined by the end of the rib or ribs towards open end of the chamber when the dispenser is at rest and during actuation of the dispenser.

8. A method of affixing an add-on component, said component being substantially cylindrical, onto a dispensing canister comprising a substantially cylindrical container having a closed end and an open end, said open end of the container being equipped by means of a ferrule with a dispensing means, said method comprising the following steps:

a) positioning the add-on component adjacent to the closed end of the container to form a generally cylindrical canister-component sub-assembly having an interface between the canister and add-on component;

b) providing an adhesive-backed film; and c) mounting an adhesive-backed film circumferentially about the canister-component sub-assembly and adhering the adhesive-backed film to an external surface of the container and an external surface of the add-on component, such that the upper edge of the film is located about the add-on component and the lower edge of the film about the container in the vicinity of the upper edge of the ferrule, and such that the first section of the film extends across the canister-component interface with the first end region of the first section of the film overlapping the second end region of the first section of the film, while the end regions of the second section of the film do not overlap.

* * * * *